(12) United States Patent
Fukuda et al.

(10) Patent No.: US 10,642,556 B2
(45) Date of Patent: May 5, 2020

(54) IMAGE FORMING APPARATUS CAPABLE OF COMMUNICATING WITH A MODALITY

(71) Applicant: Oki Data Corporation, Minato-ku, Tokyo (JP)

(72) Inventors: Takafumi Fukuda, Tokyo (JP); Patrick Rabel, Rungis (FR)

(73) Assignee: Oki Data Corporation, Tokyo (JP)

( * ) Notice: Subject to any disclaimer, the term of this patent is extended or adjusted under 35 U.S.C. 154(b) by 111 days.

(21) Appl. No.: 15/492,177

(22) Filed: Apr. 20, 2017

(65) Prior Publication Data

US 2017/0337021 A1 Nov. 23, 2017

(30) Foreign Application Priority Data

May 18, 2016 (JP) ................... 2016-099244

(51) Int. Cl.
| | |
|---|---|
| *H04N 1/00* | (2006.01) |
| *G06F 3/12* | (2006.01) |
| *H04N 1/21* | (2006.01) |
| *A61B 5/00* | (2006.01) |
| *H04N 1/23* | (2006.01) |
| *G06F 19/00* | (2018.01) |
| *G01R 33/54* | (2006.01) |

(52) U.S. Cl.
CPC .............. *G06F 3/1268* (2013.01); *A61B 5/00* (2013.01); *G06F 3/1236* (2013.01); *G06F 19/321* (2013.01); *H04N 1/00* (2013.01); *H04N 1/00127* (2013.01); *H04N 1/00244* (2013.01); *H04N 1/00249* (2013.01); *H04N 1/00408* (2013.01); *H04N 1/00525* (2013.01); *H04N 1/21* (2013.01); *H04N 1/2338* (2013.01); *G01R 33/543* (2013.01); *H04N 2201/0079* (2013.01); *H04N 2201/0081* (2013.01); *H04N 2201/0094* (2013.01); *H04N 2201/3223* (2013.01)

(58) Field of Classification Search
None
See application file for complete search history.

(56) References Cited

U.S. PATENT DOCUMENTS

| | | | |
|---|---|---|---|
| 8,527,617 B2 * | 9/2013 | Nakano | G06F 19/321 382/128 |
| 2009/0316013 A1 * | 12/2009 | Largent | H04N 1/2179 348/222.1 |

(Continued)

FOREIGN PATENT DOCUMENTS

| | | |
|---|---|---|
| CN | 1315714 A | 10/2001 |
| EP | 1217819 A2 | 6/2002 |
| JP | 2001094744 A | 4/2001 |

OTHER PUBLICATIONS

English Translation of Masashi, JP 2001-094744 (Year: 2001).*

*Primary Examiner* — Mohammad H Ghayour
*Assistant Examiner* — Pawan Dhingra
(74) *Attorney, Agent, or Firm* — Panitch Schwarze Belisario & Nadel LLP

(57) ABSTRACT

An image forming apparatus includes: a memory that stores a setting for a first process in association with an identifier; a receiver that receives the identifier, image data, and a request for a second process from a host apparatus capable of requesting the second process but incapable of requesting the first process; and a processor that performs the first process on a basis of the image data according to the setting stored in association with the identifier.

14 Claims, 14 Drawing Sheets

(56) References Cited

U.S. PATENT DOCUMENTS

2011/0292445 A1\* 12/2011 Kato ................... G06F 3/1222
 358/1.15
2014/0188515 A1\* 7/2014 Mansker ............... G06F 19/321
 705/3

\* cited by examiner

FIG. 10

| UID | UID NAME | Storage ATTRIBUTE |
|---|---|---|
| 1.2.840.10008.5.1.9 | Basic Grayscale Print Management Meta SOP Class | FALSE |
| 1.2.840.10008.5.1.18 | Basic Color Print Management Meta SOP Class | FALSE |
| 1.2.840.10008.5.1.16 | Printer SOP Class | FALSE |
| 1.2.840.10008.5.1.23 | Presentation LUT SOP Class | FALSE |
| 1.2.840.10008.5.1.1 | Basic Film Session SOP Class | FALSE |
| 1.2.840.10008.5.1.2 | Basic Film Box SOP Class | FALSE |
| 1.2.840.10008.5.1.4 | Basic Grayscale Image Box SOP Class | FALSE |
| 1.2.840.10008.5.1.4.1 | Basic Color Image Box SOP Class | FALSE |
| 1.2.840.10008.1.1 | Verification SOP Class | FALSE |
| 1.2.840.10008.5.1.4.1.1.2 | CT Image Storage | TRUE |
| 1.2.840.10008.5.1.4.1.1.4 | MR Image Storage | TRUE |
| 1.2.840.10008.5.1.4.1.1.6.1 | Ultrasound Image Storage | TRUE |
| 1.2.840.10008.5.1.1.7 | Scondary Capture Image Storage | TRUE |
| 1.2.840.10008.5.1.1.77.1.5.1 | Ophthalmic Photography 8 bit Image Storage | TRUE |

IMAGE FORMING APPARATUS CAPABLE OF COMMUNICATING WITH A MODALITY

BACKGROUND OF THE INVENTION

1. Field of the Invention

The present invention relates to an image forming apparatus, and more particularly, to an image forming apparatus that performs a process in response to a request from a host apparatus.

2. Description of the Related Art

In the Digital Imaging and Communication in Medicine (DICOM) standard, a modality can capture medical image data and send the image data to an image forming apparatus to print the image data. However, when a user uses a modality having no Print Service Class User (SCU) function, the user needs to send (and store) medical image data to (and in) a medical image server having a Print SCU function by using a Storage SCU function, and then perform DICOM print operation at the medical image server.

For example, Japanese Patent Application Publication No. 2001-94744 discloses a system in which a modality sends image data to an image server, which stores the image data and forwards the image data to a printer, which prints the image data.

However, a conventional image forming apparatus cannot perform a process in response to a request from a host apparatus incapable of requesting the process.

SUMMARY OF THE INVENTION

An aspect of the present invention is intended to provide an image forming apparatus capable of performing a process in response to a request from a host apparatus incapable of requesting the process.

According to an aspect of the present invention, there is provided an image forming apparatus including: a memory that stores a setting for a first process in association with an identifier; a receiver that receives the identifier, image data, and a request for a second process from a host apparatus capable of requesting the second process but incapable of requesting the first process; and a processor that performs the first process on a basis of the image data according to the setting stored in association with the identifier.

BRIEF DESCRIPTION OF THE DRAWINGS

In the attached drawings:

FIG. 10 schematically illustrates an example of an abstract syntax list;

DETAILED DESCRIPTION OF THE INVENTION

<Configuration>

Figure 1:
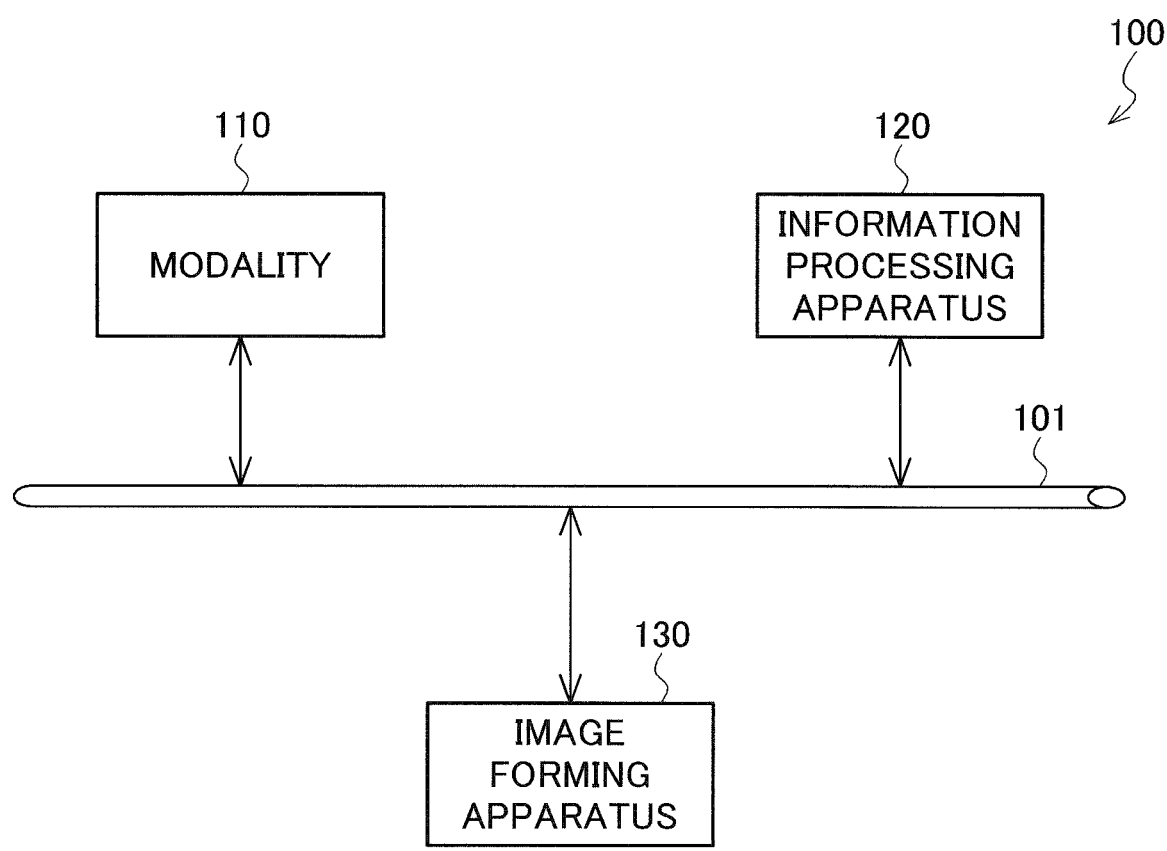
FIG. 1 is a schematic diagram of an image forming system.

FIG. 1 is a schematic diagram of an image forming system 100 according to an embodiment.

The image forming system 100 includes a modality 110 as a host apparatus, an information processing apparatus 120, and an image forming apparatus 130.

The modality 110, information processing apparatus 120, and image forming apparatus 130 are connected to a network 101.

The modality 110 is an apparatus capable of generating medical image data according to the Digital Imaging and Communication in Medicine (DICOM) standard and transmitting the medical image data to a predetermined system or image forming apparatus according to DICOM standard interface. The modality 110 is, for example, an ultrasonic diagnostic apparatus, a computed tomography (CT) apparatus, or the like.

The information processing apparatus 120 includes a web browser capable of displaying data sent according to HyperText Transfer Protocol (HTTP).

Figure 2:
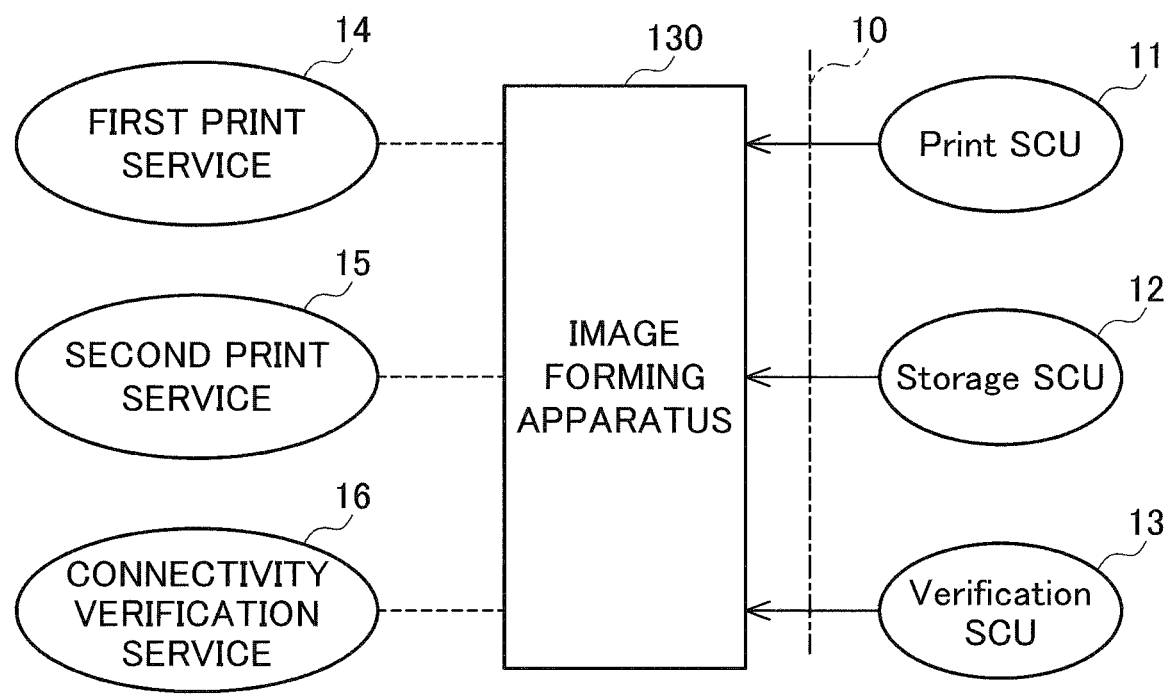
FIG. 2 is an implementation model diagram of an image forming apparatus.

FIG. 2 is an implementation model diagram of the image forming apparatus 130.

The image forming apparatus 130 provides a first print service 14 of receiving a print request (or image formation request) including image data and print parameters (or image formation parameters) from a Print Service Class User (SCU) 11 through a DICOM standard interface 10 and performing printing (or image formation).

The image forming apparatus 130 also provides a second print service 15 of receiving a storage request (including image data, examination information, patient information, or the like) from a Storage SCU 12 through the DICOM standard interface 10 and performing printing on the basis of settings of an Application Entity Title (AET).

The image forming apparatus 130 further provides a connectivity verification service 16 of receiving a connectivity verification request from a Verification SCU 13 through the DICOM standard interface 10 and performing connectivity verification.

Figure 3:
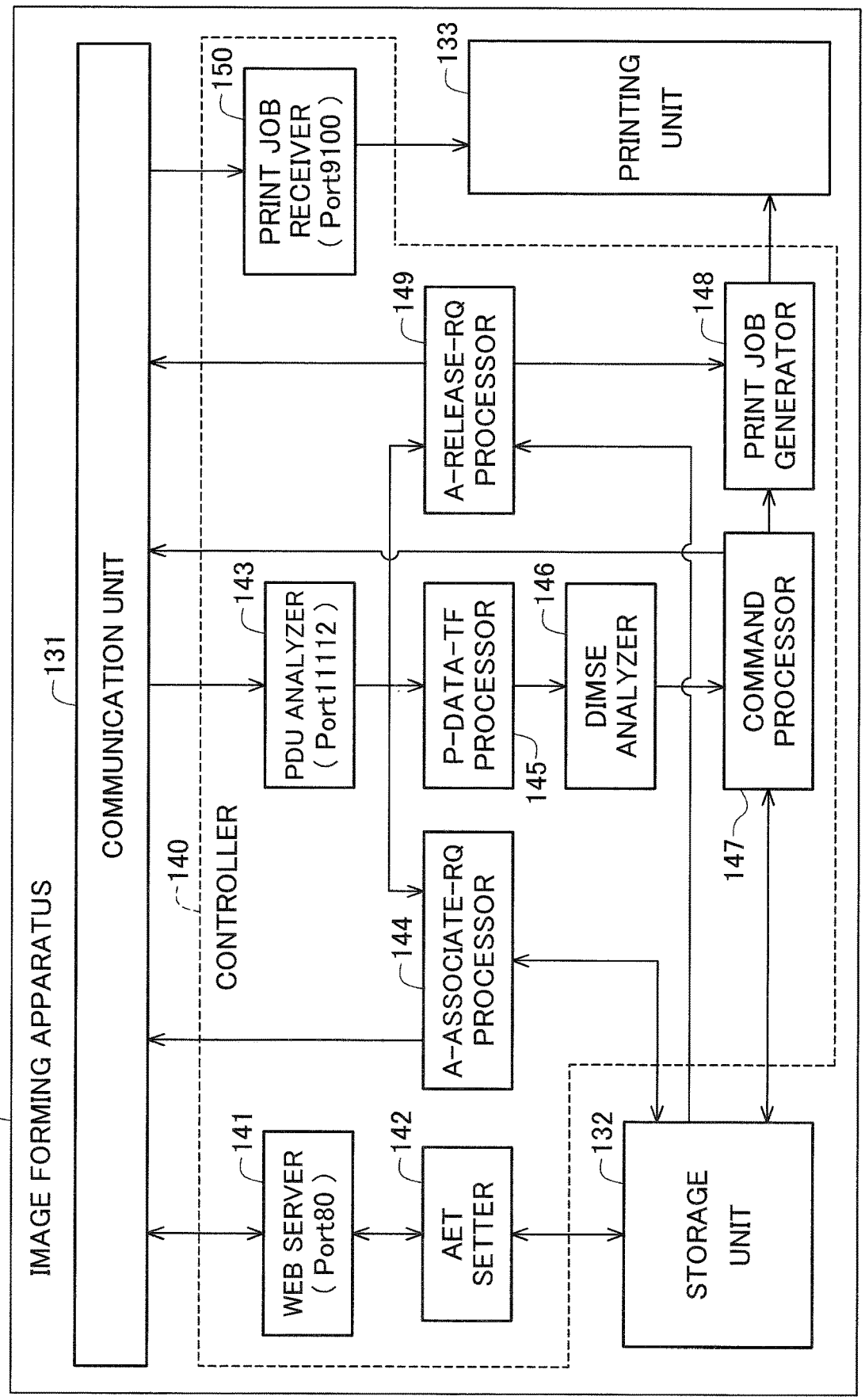
FIG. 3 is a block diagram schematically illustrating a configuration of the image forming apparatus.

FIG. 3 is a block diagram schematically illustrating a configuration of the image forming apparatus 130.

The image forming apparatus 130 includes a communication unit (or communication interface) 131, a storage unit (or memory) 132, a printing unit (or printer) 133 as an image forming unit, and a controller 140.

The controller 140 and printing unit 133 function as a processor (or process executing unit) that performs, instead of a first process requested by a host apparatus, a second process on the basis of image data according to one or more settings (or process content items) corresponding to an identifier (or identification information) sent from the host apparatus. In this embodiment, the first process is a process of storing data, and the second process is a process of forming an image on a medium.

The communication unit 131 communicates with the modality 110 and information processing apparatus 120 through the Transmission Control Protocol/Internet Protocol (TCP/IP) network 101 according to TCP/IP protocol. For example, the communication unit 131 functions as a receiver that receives an identifier (or identification information) corresponding to one or more settings (or process content items) for the second process, image data, and a request for storage of data from the modality 110. When receiving a connection request, the communication unit 131 passes processing to a subsequent unit corresponding to a port number to which the connection request is directed. For example, when the communication unit 131 receives data specifying a port number "80", it provides the data to the web server 141, which is assigned the port number "80". When the communication unit 131 receives data specifying a port number "11112", it provides the data to the PDU analyzer 143, which is assigned the port number "11112". When the communication unit 131 receives data specifying a port number "9100", it provides the data to the print job receiver 150, which is assigned the port number "9100".

The storage unit 132 stores data required for processing by the image forming apparatus 130. For example, the storage unit 132 stores one or more settings (or process content items) for a process of forming an image on a medium in association with an identifier (or identification information).

The printing unit 133 processes a print job (or image formation job) processed by the controller 140 and performs printing (or image formation).

The controller 140 controls processing in the image forming apparatus 130.

The controller 140 includes a web server 141, an AET setter 142, a PDU analyzer 143, an A-ASSOCIATE-RQ processor 144, a P-DATA-TF processor 145, a DIMSE analyzer 146, a command processor 147, a print job generator 148 as an image formation job generator, an A-RELEASE-RQ processor 149, and a print job receiver 150.

The web server 141 provides a web service to the web browser of the information processing apparatus 120 through the communication unit 131 using HTTP.

The AET setter 142 makes settings regarding AET through the web server 141.

The PDU analyzer 143 receives, through the communication unit 131, data sent from the modality 110 through the DICOM standard interface 10, analyzes a Protocol Data Unit (PDU) included in the data, and passes processing to a subsequent processor on the basis of the analysis.

The A-ASSOCIATE-RQ processor 144 examines an A-ASSOCIATE-RQ PDU, which is an association establishment request, provided from the PDU analyzer 143, and sends a response to the modality 110 (i.e., requestor) through the communication unit 131 on the basis of the examination.

The P-DATA-TF processor 145 examines a P-DATA-TF PDU (for DICOM message exchange) provided from the PDU analyzer 143, and passes processing to a subsequent processor on the basis of the examination.

The DIMSE analyzer 146 analyzes a DICOM Message Service Element (DIMSE) in a DICOM message provided from the P-DATA-TF processor 145 to acquire a command thereof.

The command processor 147 processes commands acquired by the DIMSE analyzer 146, and sends a response to the modality 110 (i.e., requestor) through the communication unit 131.

The print job generator 148 generates a print job using a page description language (PDL) on the basis of image data that is sent from the modality 110 and stored in the image forming apparatus 130 (e.g., the storage unit 132) by the command processor 147.

The A-RELEASE-RQ processor 149 examines an A-RELEASE-RQ PDU, which is an association release request, provided from the PDU analyzer 143, and sends, to the modality 110 (i.e., requestor) through the communication unit 131, a response depending on the examination.

The print job receiver 150 receives, through the communication unit 131, a print job generated by a printer driver in the information processing apparatus 120, and passes the print job to a subsequent processor.

<Operation>

Conventionally, analog images, such as film images, have been used for medical image diagnosis (e.g., X-ray diagnosis). However, in recent years, digital image data has been widely used. As a major method of using digital image data, there is a method of generating data compliant with the DICOM standard including digital image data and associated information, such as patient information and image acquisition date information, sending and receiving the data through a network according to the DICOM standard, and displaying the data on a high-resolution monitor for diagnosis.

In this method, image data captured by modalities is sent to picture archiving and communication systems (PACSs) and stored therein. The image data stored in the PACSs is acquired by modalities or image viewing programs (or viewers) compliant with the DICOM standard, if necessary.

In the above method, the modalities are required to have a function of sending captured image data (or Storage SCU), and some modalities have only this function for cost reduction.

Medical image data may also be printed as explanatory material for informed consent or material for a conference. In such a case, when a user uses a modality having a function of requesting printing of image data (or Print SCU), the user can operate the modality to request printing. However, when a user uses a modality having no function of requesting printing (or Print SCU), the user needs to send image data from the modality to a PACS and then operate a terminal of the PACS to request printing of the image data. This is based on storing image data in a PACS. Thus, captured image data cannot be printed when the PACS is down due to failure, maintenance, or other reasons, when the PACS has a small storage capacity, or when there is no PACS in a system. Further, since the user needs to operate the modality 110 and then operate the PACS, it takes effort to print image data.

To address such problems, in this embodiment, a Storage SCU sends image data to the image forming apparatus 130, specifying a preset AET. Thereby, the image forming apparatus 130 can generate a print job according to settings (or a format) specified when the AET is set, and print it. Further, when receiving a request from a Print SCU, the image forming apparatus 130 can generate a print job according to requested settings (or format) and print it.

Next, setting of an AET will be described.

When an SCU establishes connection with a Service Class Provider (SCP) according to the DICOM standard, the SCU sends the SCP a request specifying an AET provided by the SCP. In this embodiment, the information processing apparatus 120 can preset information for an AET provided by the SCP, by accessing, from the web browser, a URL provided by the web server 141 of the image forming apparatus 130.

Figure 4:
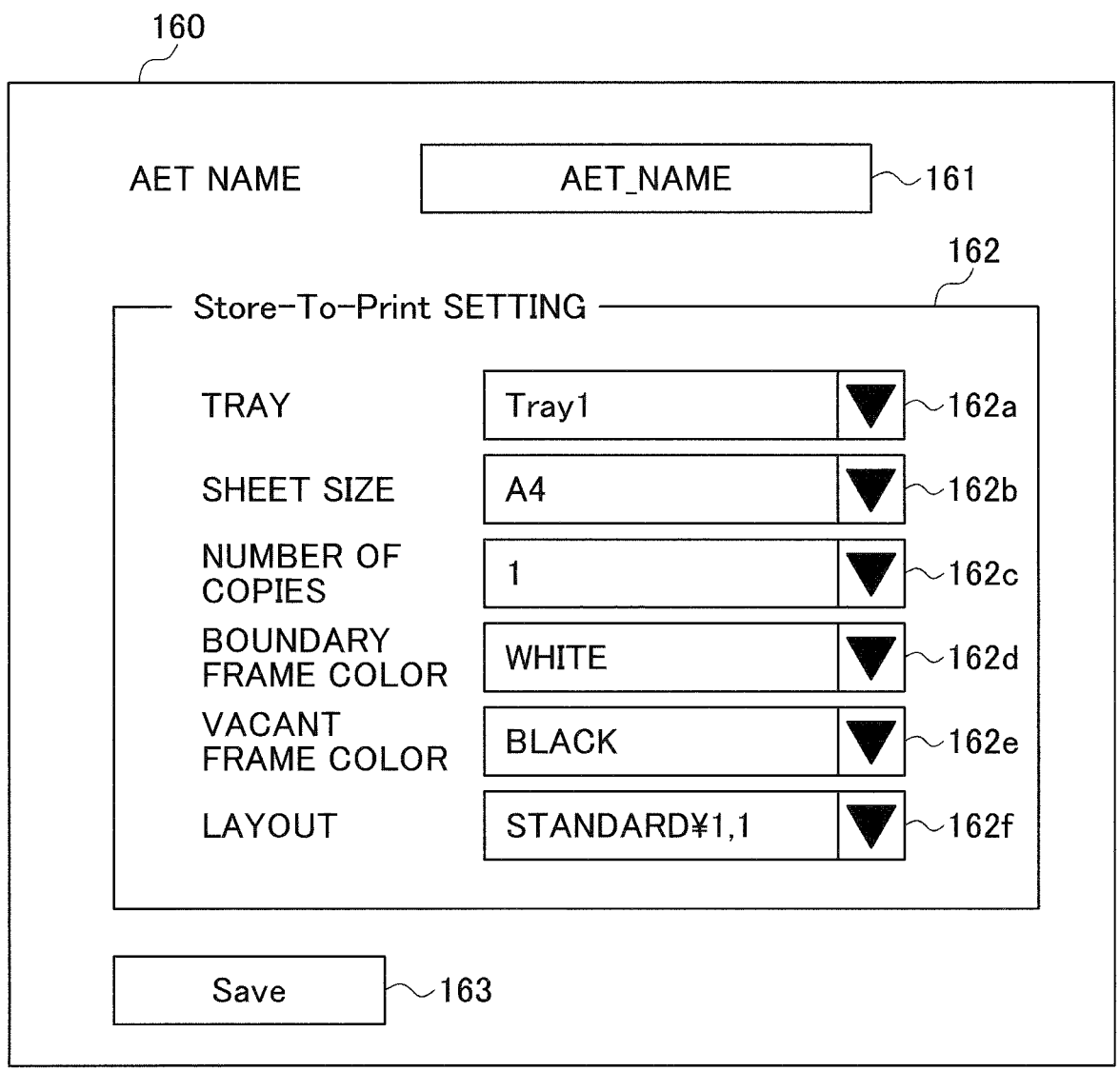
FIG. 4 is a schematic view illustrating an AET setting screen.

FIG. 4 is a schematic view illustrating an AET setting screen 160 in this embodiment.

In the AET setting screen 160, information for an AET is set.

The AET setting screen 160 includes an AET name input field 161, Store-To-Print setting input field 162, and a Save button 163.

The AET name input field 161 is a field for receiving input of an AET name, which is an identifier (or identification information) for identifying an AET. The AET name is an arbitrary character string. When the image forming apparatus 130 holds multiple AETs, each AET name is unique in the image forming apparatus 130.

The Store-To-Print setting input field 162 is a field for receiving input of print settings (or image formation settings), which are settings to be used when a request specifying the AET name input in the AET name input field 161 is received from a Storage SCU. A Storage SCU is intended to send (and store) image data, and thus sends no parameters required for printing, unlike a Print SCU. Thus, parameters to be used when a request from a Storage SCU is received are set in advance.

In this embodiment, the Store-To-Print setting input field 162 includes a tray selection field 162a, a sheet size selection field 162b, a number of copies selection field 162c, a boundary frame color selection field 162d, a vacant frame color selection field 162e, and a layout selection field 162f. In the Store-To-Print setting input field 162 of this embodiment, a tray, a sheet size, the number of copies, a boundary frame color, a vacant frame color, and a layout can be specified as print settings in the fields 162a to 162f. Other print settings or parameters may be specified.

In the tray selection field 162a, a sheet tray storing media to be used for printing is selected.

The sheet size selection field 162b is available when a multi-purpose (MP) tray is selected in the tray selection field 162a. In the sheet size selection field 162b, the size of a medium to be set on the MP tray is selected.

In the number of copies selection field 162c, the number of copies to be printed is selected.

When a layout in which multiple images are allocated to a page is selected in the layout selection field 162f, in the boundary frame color selection field 162d, the color of the boundary between images is selected from black and white.

Figure 5A:
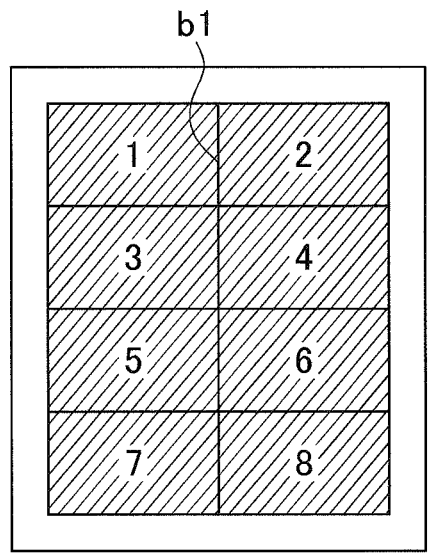
FIGS. 5A and 5B are schematic views for explaining a boundary frame color.

When black is selected in the boundary frame color selection field 162d, the boundary b1 between images is printed in black as illustrated in FIG. 5A.

Figure 5B:
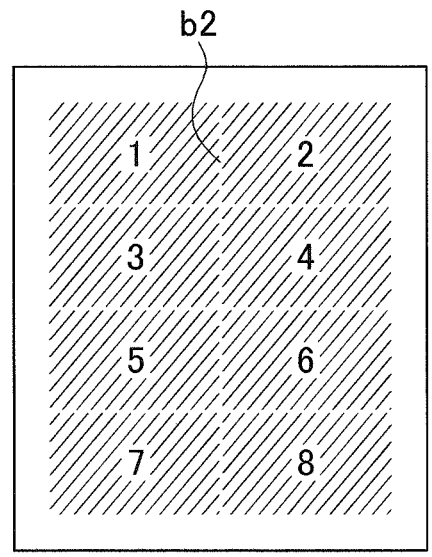

When white is selected in the boundary frame color selection field 162d, the boundary b2 between images is printed in white as illustrated in FIG. 5B.

Referring back to FIG. 4, when a layout in which multiple images are allocated to a page is selected in the layout selection field 162f, in the vacant frame color selection field 162e, the color of vacant frames to which no image is allocated is selected from white and black.

Figure 6A:
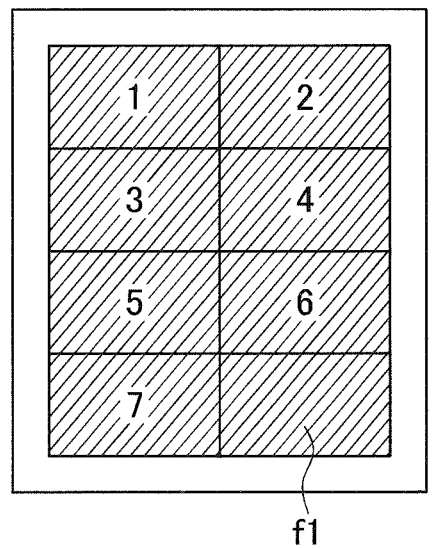
FIGS. 6A and 6B are schematic views for explaining a vacant frame color.
Figure 6B:
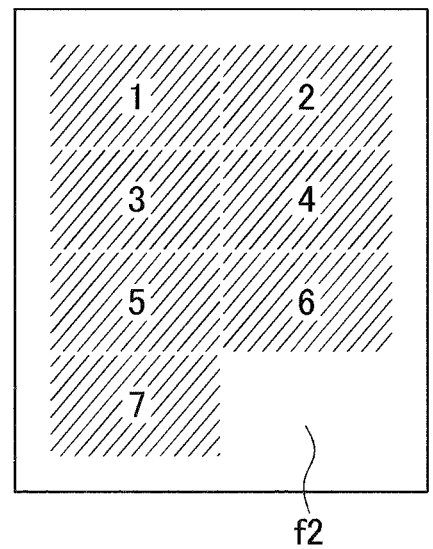

When black is selected in the vacant frame color selection field 162e, a vacant frame f1 is printed in black as illustrated in FIG. 6A. When white is selected in the vacant frame color selection field 162e, a vacant frame f2 is printed in white as illustrated in FIG. 6B.

Referring back to FIG. 4, in the layout selection field 162f, the layout of one or more images in a page is selected from among multiple layouts. Each of the multiple layouts is identified by a layout name consisting of a character string "STANDARD", a mark "¥", and variables C (or Column) and R (or Row).

FIGS. 7A to 7G are schematic views illustrating an example of the layouts that are selectable in the layout selection field 162f.

Figure 7A:
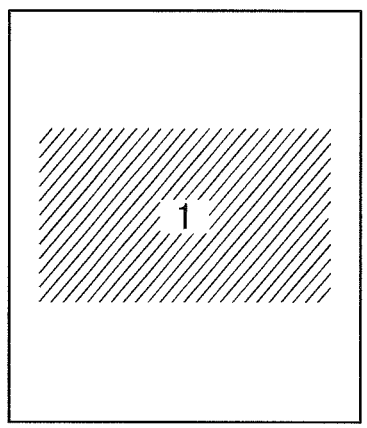
FIGS. 7A to 7G are schematic views illustrating an example of layouts.
Figure 7B:
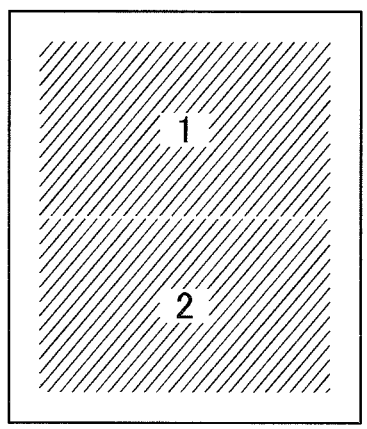
Figure 7C:
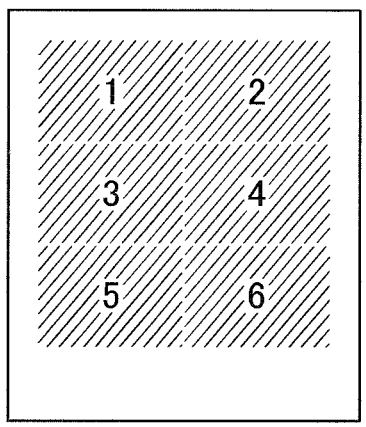
Figure 7D:
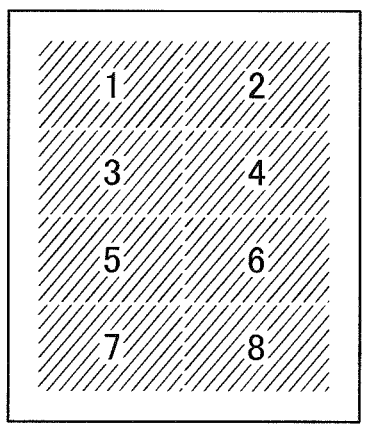
Figure 7E:
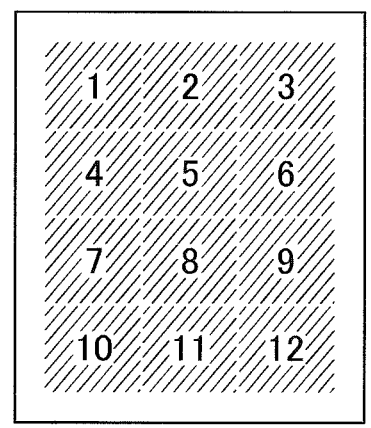
Figure 7F:
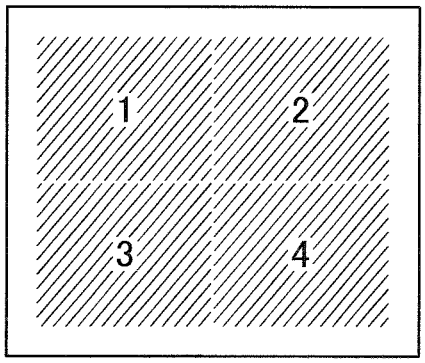
Figure 7G:
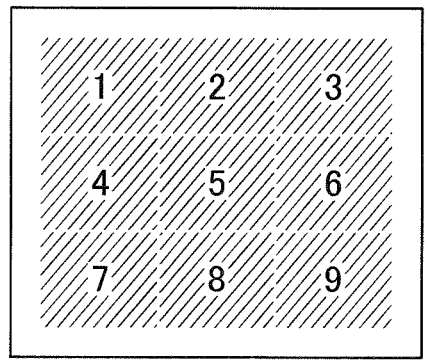

FIG. 7A illustrates a layout having a layout name "STANDARD¥1,1", in which one image is allocated to a page. FIG. 7B illustrates a layout having a layout name "STANDARD¥1,2", in which two images are allocated to a page. FIG. 7C illustrates a layout having a layout name "STANDARD¥2,3", in which six images are allocated to a page. FIG. 7D illustrates a layout having a layout name "STANDARD¥2,4", in which eight images are allocated to a page. FIG. 7E illustrates a layout having a layout name "STANDARD¥3,4", in which twelve images are allocated to a page. FIG. 7F illustrates a layout having a layout name "STANDARD¥2,2", in which four images are allocated to a page. FIG. 7G illustrates a layout having a layout name "STANDARD¥3,3", in which nine images are allocated to a page.

To minimize image size reduction, for "STANDARD¥1,1", "STANDARD¥1,2", "STANDARD¥2,3", "STANDARD¥2,4", and "STANDARD¥3,4", the medium orientation is portrait; for "STANDARD¥2,2" and "STANDARD¥3,3", the medium orientation is landscape.

Referring back to FIG. 4, the Save button 163 is a button for receiving input of an instruction to store print settings input in the Store-To-Print setting input field 162 in association with an AET name input in the AET name input field 161. When the instruction is input using the Save button 163 (or when the Save button 163 is pressed), print settings input in the Store-To-Print setting input field 162 are stored in the storage unit 132 in association with an AET name input in the AET name input field 161. For example, the image forming apparatus 130 holds one or more AETs in advance, and when receiving an AET name and print settings corresponding to one of the AETs through the AET setting screen 160, stores the received AET name and print settings in association with the corresponding AET.

Next, a process in which a Storage SCU issues a request to the image forming apparatus 130 and the image forming apparatus 130 receives image data and prints the image data will be described. In this example, the modality 110 has no Print SCU, and causes the image forming apparatus 130 to perform printing, using a Storage SCU. In other words, since the modality 110 cannot request printing to the image forming apparatus 130, the modality 110 causes the image forming apparatus 130 to perform printing based on image data, by requesting storage of the image data.

Figure 8:
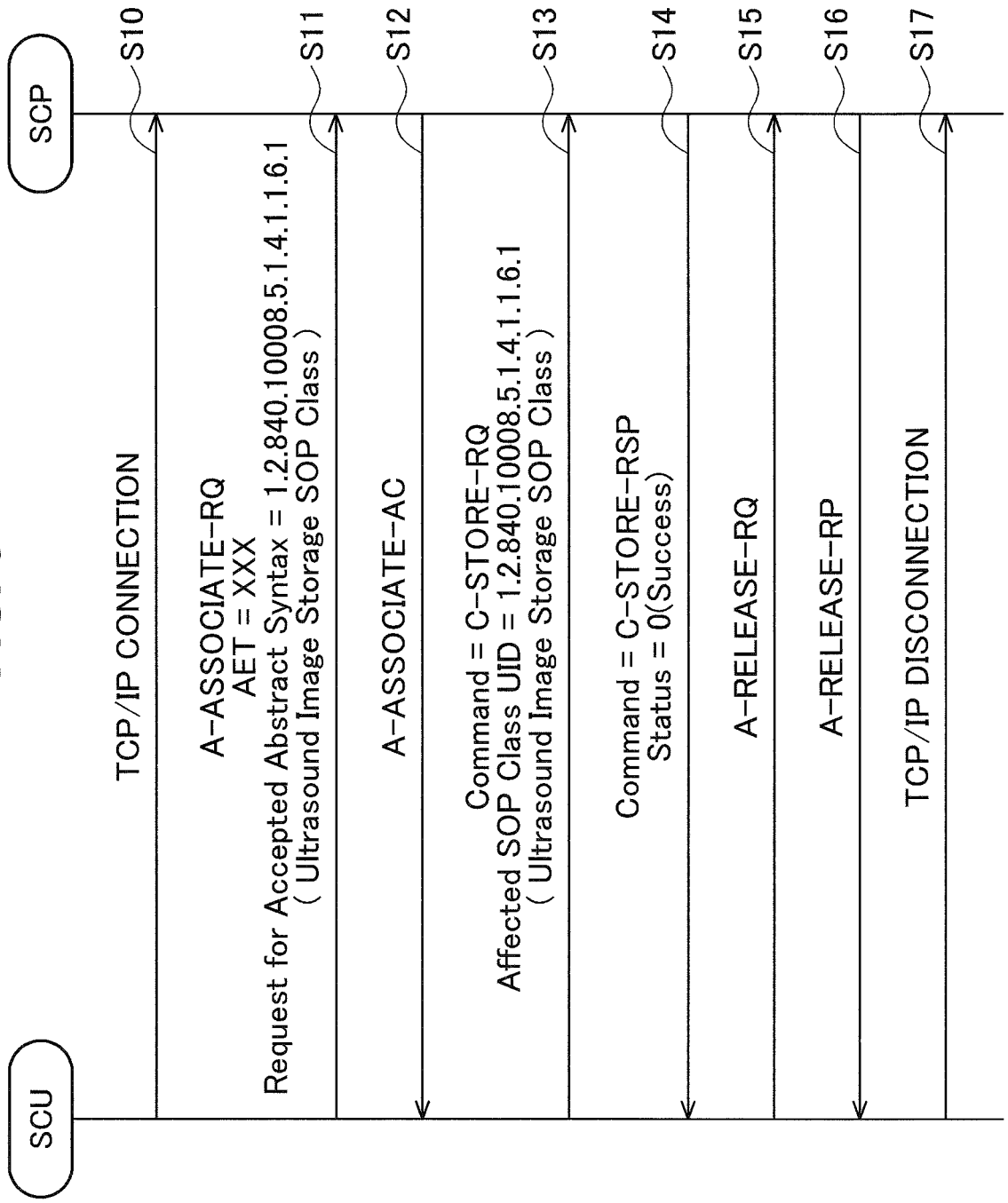
FIG. 8 is a sequence diagram illustrating a process between a Storage SCU and a SCP.

FIG. 8 is a sequence diagram illustrating a process between a Storage SCU and an SCP.

For example, the Storage SCU is the modality 110, and the SCP is the image forming apparatus 130. FIG. 8 illustrates, as an example, a sequence in which the modality 110 is an ultrasonic diagnostic apparatus and sends image data of an ultrasound image to the image forming apparatus 130.

First, the SCU issues a TCP/IP connection request specifying an IP address and a port number to the SCP, and the SCP accepts the request, so that a TCP/IP connection is established (S10).

The SCU sends an A-ASSOCIATE-RQ PDU, which is an association establishment request, using the established connection (S11). At this time, the A-ASSOCIATE-RQ PDU includes an AET name and one or more requested application contexts. When the Storage SCU requests printing to the image forming apparatus 130, it includes an AET name preset using the AET setting screen 160 illustrated in FIG. 4 in the A-ASSOCIATE-RQ PDU.

FIG. 8 shows an application context "1.2.840.10008.5.1.4.1.1.6.1", which is defined as the Service-Object Pair (SOP) Class UID for Ultrasound Image Storage in the DICOM standard.

If the AET requested in step S11 is present and the application context is acceptable, the SCP sends an A-ASSOCIATE-AC PDU, which is a positive response, to the SCU (S12).

If the requested AET is not present or when the application context is not acceptable, the SCP sends an A-ASSOCIATE-RJ PDU, which is a negative response, to the SCU, and the SCU releases the connection.

The description will continue on the assumption that the requested AET is present and the application context is acceptable.

Next, the SCU sends command information (group 0000), examination information (group 0008), patient information (group 0010), image acquisition information (groups 0018 and 0020), and image data (group 7ef0) in the DIMSE format using P-DATA-TF PDUs (S13). Here, the command type (0000,0100) included in the command information is set to "0001H" for the C-STORE-RQ message, which indicates a request for storage.

Upon receipt of the information sent from the SCU, the SCP processes the sent information (in many cases, stores the sent information into a storage), and sends the SCU a response in which the command type is set to "8001H" for the C-STORE-RSP message and the status (0000,0900) is set to "0", which indicates a normal end (S14).

When there are multiple image data items, the steps S13 and S14 are repeated.

Upon completion of sending image data to be processed, the SCU sends an A-RELEASE-RQ PDU, which is an association release request, to the SCP (S15).

Upon receipt of the association release request, the SCP sends an A-RELEASE-RP PDU, which is an association release request response, to the SCU (S16).

Upon receipt of the response, the SCU disconnects the established TCP/IP connection, and the process finishes (S17).

Next, a process by the A-ASSOCIATE-RQ processor 144 will be described.

Figure 9:
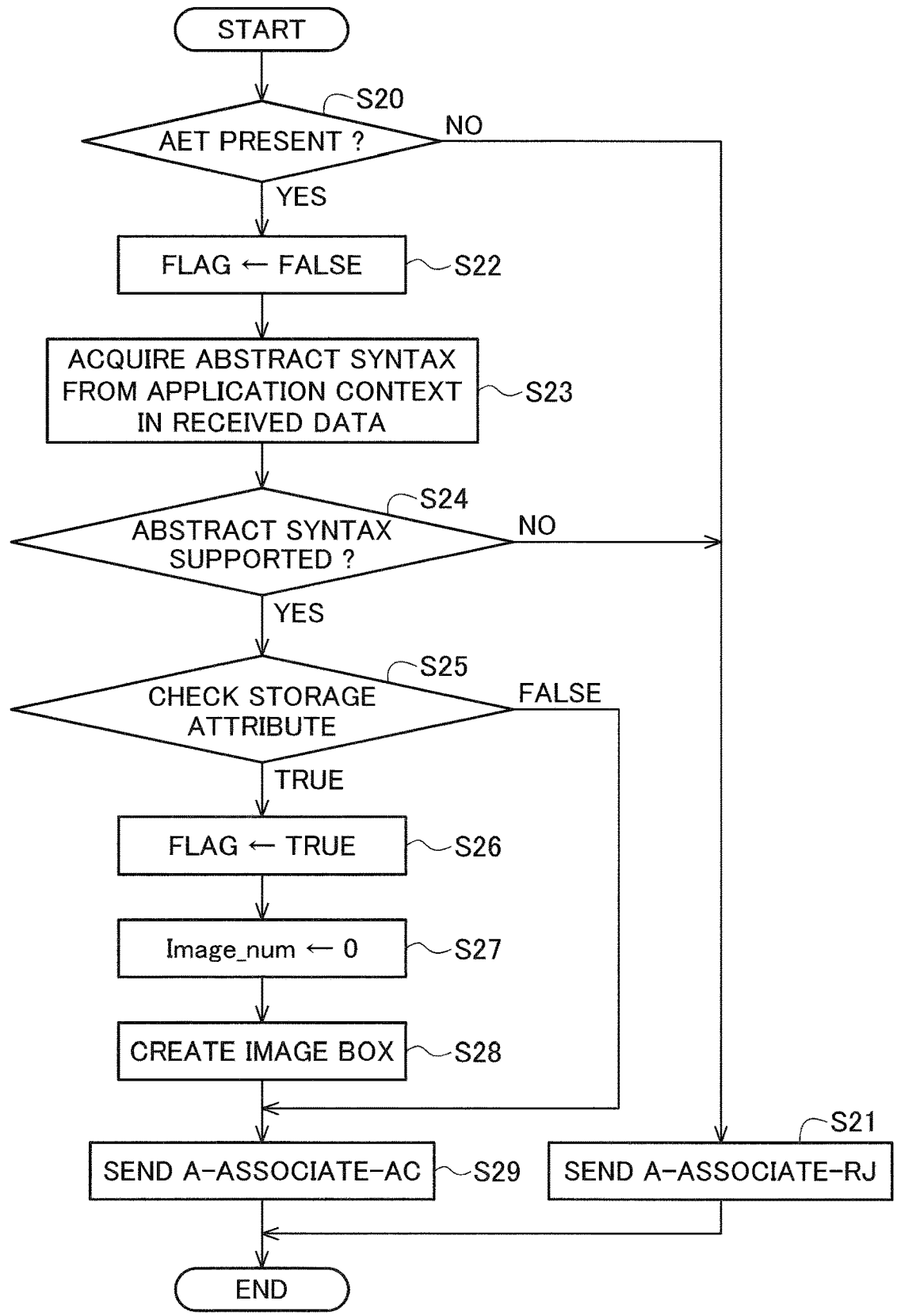
FIG. 9 is a flowchart illustrating a process of an A-ASSOCIATE-RQ processor.

FIG. 9 is a flowchart illustrating the process by the A-ASSOCIATE-RQ processor 144.

First, the A-ASSOCIATE-RQ processor 144 determines whether an AET requested by the modality 110 as an SCU is defined in the image forming apparatus 130 (S20). Specifically, if an AET name included in an A-ASSOCIATE-RQ PDU sent from the modality 110 is stored in the storage unit 132, the A-ASSOCIATE-RQ processor 144 determines that the AET requested by the SCU is defined in the image forming apparatus 130. If the AET requested by the SCU is not defined in the image forming apparatus 130 (NO in step S20), the process proceeds to step S21. If the AET requested by the SCU is defined in the image forming apparatus 130 (YES in step S20), the process proceeds to step S22.

In step S21, the A-ASSOCIATE-RQ processor 144 sends an A-ASSOCIATE-RJ PDU, which is a negative response, to the requesting SCU, and then the process ends. Thereby, the controller 140 rejects reception of image data through the communication unit 131.

In step S22, the A-ASSOCIATE-RQ processor 144 resets an internal flag indicating whether the request is from a Storage SCU to an initial value "FALSE". The internal flag is stored in, for example, the storage unit 132.

The A-ASSOCIATE-RQ processor 144 then acquires an abstract syntax from an application context included in the A-ASSOCIATE-RQ PDU sent from the modality 110 (S23).

The A-ASSOCIATE-RQ processor 144 then determines whether the abstract syntax acquired in step S23 is supported by the image forming apparatus 130 (S24). For example, the storage unit 132 previously stores an abstract syntax list listing abstract syntaxes supported by the image forming apparatus 130, and the A-ASSOCIATE-RQ processor 144 determines whether the abstract syntax acquired in step S23 is present in the abstract syntax list. If the abstract syntax acquired in step S23 is supported (YES in step S24), the process proceeds to step S25. If the abstract syntax acquired in step S23 is not supported (NO in step S24), the process proceeds to step S21.

FIG. 10 schematically illustrates an example of the abstract syntax list.

In FIG. 10, the abstract syntax list 165 is information in the form of a table, and includes a UID column 165*a*, a UID name column 165*b*, and a Storage attribute column 165*c*.

The UID column 165*a* stores one or more unique identifiers (UIDs) that are abstract syntaxes supported by the image forming apparatus 130. The A-ASSOCIATE-RQ processor 144 compares the abstract syntax acquired in step S23 with the UIDs stored in the UID column 165*a*.

The UID name column 165*b* stores one or more UID names that are identification information items for identifying UIDs stored in the UID column 165*a*. The UID names are used as character strings for log output.

The Storage attribute column 165*c* stores, for each of the UIDs stored in the UID column 165*a*, a value "TRUE" if the UID is requested by a Storage SCU, and a value "FALSE" otherwise.

In step S25, the A-ASSOCIATE-RQ processor 144 determines whether the abstract syntax acquired in step S23 is one requested by a Storage SCU. For example, the A-ASSOCIATE-RQ processor 144 determines that the abstract syntax acquired in step S23 is one requested by a Storage SCU if the value in the Storage attribute column 165*c* corresponding to the UID for the abstract syntax acquired in step S23 is "TRUE" in the abstract syntax list 165, and that the abstract syntax is not one requested by a Storage SCU if the value is "FALSE". If the abstract syntax is one requested by a Storage SCU, the process proceeds to step S26 and a process for processing a request from a Storage SCU is performed. On the other hand, if the abstract syntax is not one requested by a Storage SCU, the process proceeds to step S29.

In step S26, the A-ASSOCIATE-RQ processor 144 updates the internal flag to "True", which indicates that the request is from a Storage SCU.

The A-ASSOCIATE-RQ processor 144 then sets a variable Image_num indicating the number of image data items received from the Storage SCU, to an initial value "0" (S27).

The A-ASSOCIATE-RQ processor 144 then creates an image box for internally managing image data (S28). The image box is for storing a sequence of lists obtained by extracting image display information (data in group 0028) and pixel data (data in group 7fe0) from DIMSE data that is extracted by the DIMSE analyzer 146 from data received from the Storage SCU. Each of the lists represents an image data item.

Figure 11:
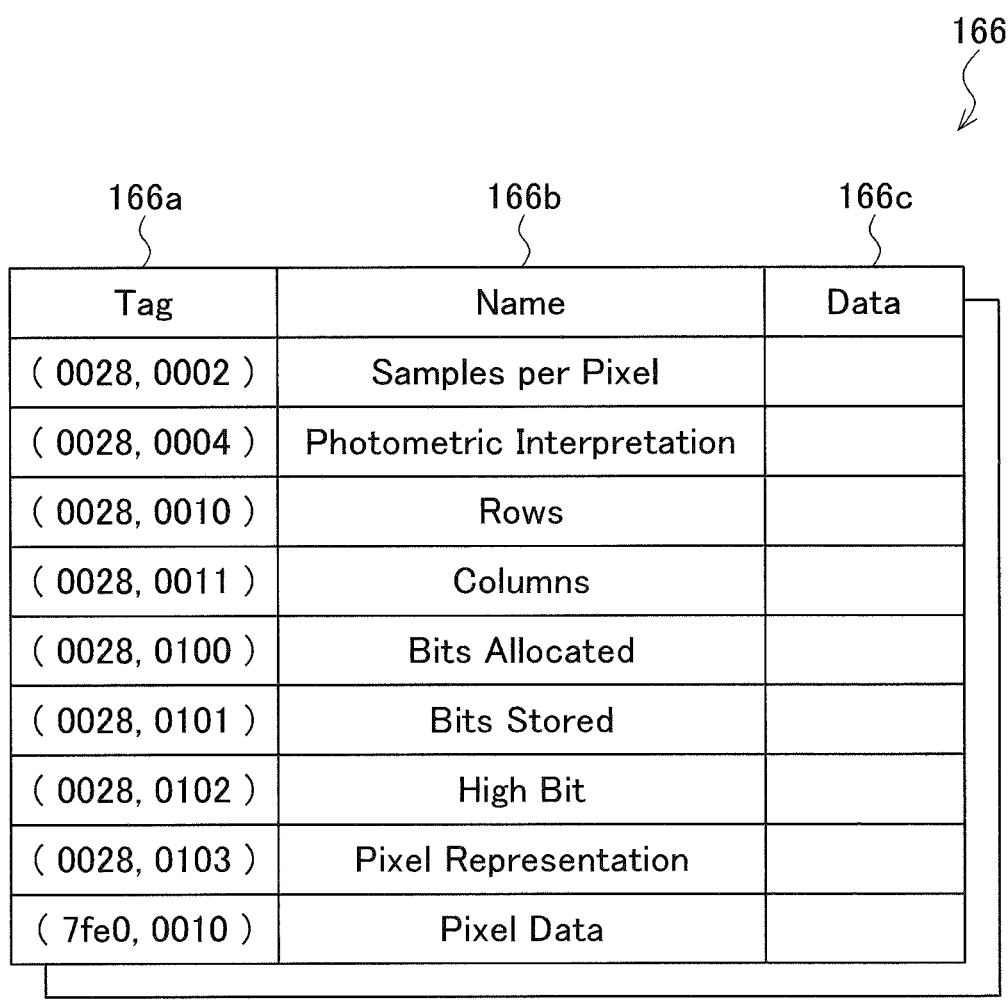
FIG. 11 schematically illustrates an example of an image box.

FIG. 11 schematically illustrates an example of the image box.

In FIG. 11, the image box 166 stores information in the form of a table, and includes a Tag column 166*a*, a Name column 166*b*, and a Data column 166*c*.

The Tag column 166a stores Tag information items required for image formation. The Tag column 166a stores the following data items defined in the DICOM standard:
- (0028,0002), indicating the number of samples per image;
- (0028,0004), indicating photometric interpretation;
- (0028,0010), indicating the number of pixels in Y-direction of the image;
- (0028,0011), indicating the number of pixels in X-direction of the image;
- (0028,0100), indicating the number of bits allocated to each pixel;
- (0028,0101), indicating the number of bits per pixel;
- (0028,0102), indicating a high bit, i.e., a most significant bit (MSB) of pixel data; and
- (7ef0,0010), indicating pixel data.

The Name column 166b stores names that are identification information items for the Tag information items stored in the Tag column 166a. The names stored in the Name column 166b are used for log output.

The Data column 166c stores data items extracted by the DIMSE analyzer 146 in association with the Tag information items stored in the Tag column 166a.

Referring back to FIG. 9, in step S29, the A-ASSOCIATE-RQ processor 144 causes the communication unit 131 to send an A-ASSOCIATE-AC PDU, which is a positive response, to the requesting SCU, and then the process ends.

Through the flow illustrated in FIG. 9, an association is established between the SCU and the SCP. After that, the SCU sends a C-STORE-RQ command to the SCP, as shown in step S13 of FIG. 8.

Next, a process performed when the image forming apparatus 130 receives the C-STORE-RQ command will be described.

Figure 12:
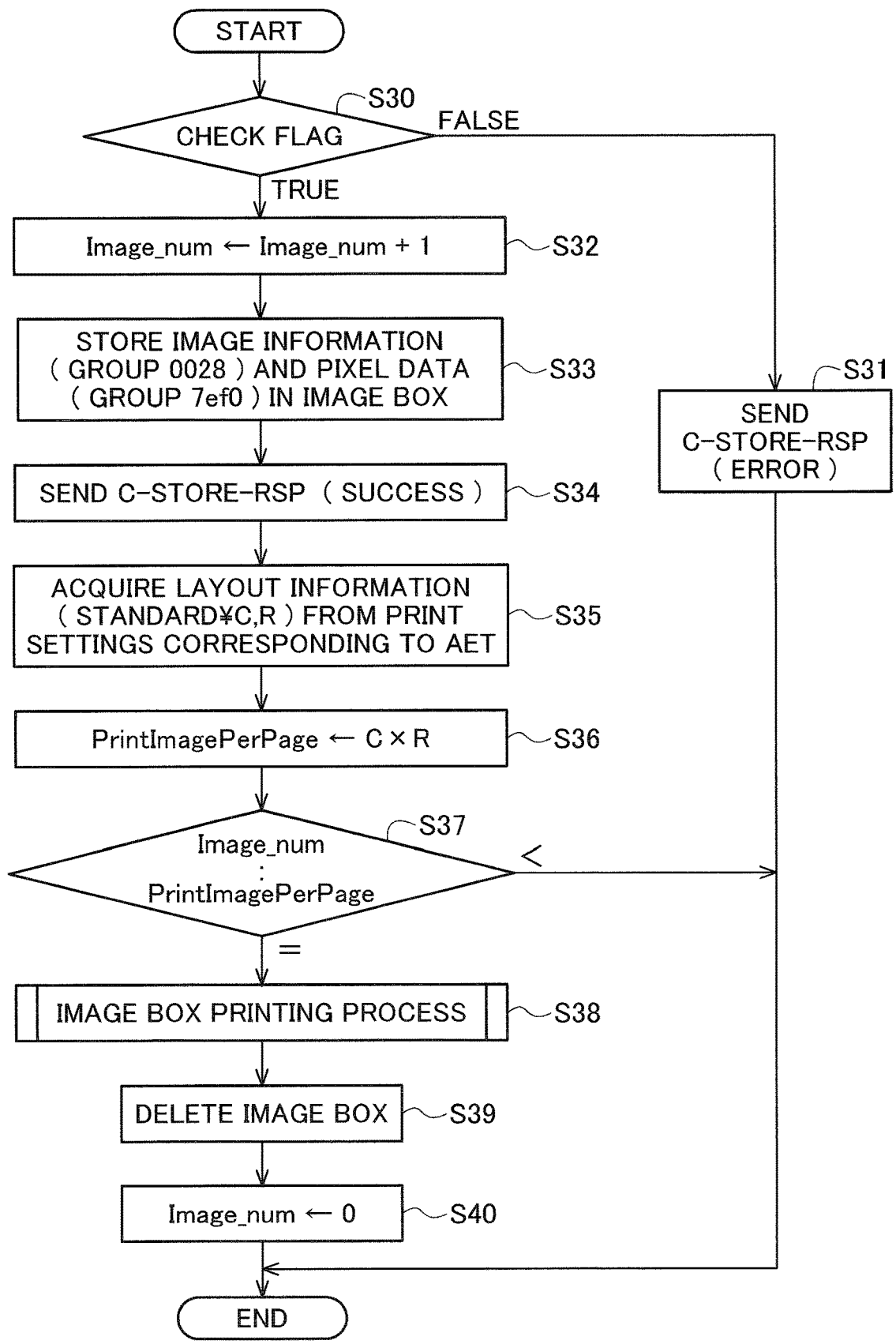
FIG. 12 is a flowchart illustrating a process by a command processor.

FIG. 12 is a flowchart illustrating a process by the command processor 147.

First, to determine whether the request is from a Storage SCU, the command processor 147 checks the internal flag indicating whether the request is from a Storage SCU (S30). If the internal flag is "False", which indicates that the request is not from a Storage SCU, the process proceeds to step S31. If the internal flag is "True", which indicates that the request is from a Storage SCU, the process proceeds to step S32.

In step S31, the command processor 147 causes the communication unit 131 to send the modality 110 a C-STORE-RSP message in which the Status is set to an error value indicating a negative response, and then the process ends.

In step S32, the command processor 147 adds 1 to the variable Image_num indicating the number of image data items received from a Storage SCU.

The command processor 147 then stores data of predetermined elements (groups 0028 and 7fe0) into the image box created in the process of the A-ASSOCIATE-RQ PDU (S33).

The command processor 147 then causes the communication unit 131 to send the modality 110 a C-STORE-RSP message in which the Status is set to a normal value "0" indicating a positive response (S34).

The command processor 147 then performs the following process to perform printing when the number of images stored in the image box reaches the number of images allocated to a page specified by the layout information.

The command processor 147 acquires the layout information (including the variables Column and Row) from the print settings stored in the storage unit 132 in association with the AET name included in the A-ASSOCIATE-RQ PDU received in step S11 of FIG. 8 (S35).

The command processor 147 then calculates, from the layout information acquired in step S35, the number of images PrintImagePerPage allocated to a page (S36). Here, the number of images PrintImagePerPage allocated to a page is obtained by multiplying Column by Row.

The command processor 147 then compares the number of images per page calculated in step S36 with the number of images that have already been stored in the image box (S37). If these two numbers are equal, the process proceeds to step S38 and printing process is performed. If the two numbers are different, the process ends without performing printing, in order to wait for reception of a subsequent image data item or an association release request.

In step S38, an image box printing process is performed. This process will be described later with reference to FIG. 14.

The command processor 147 then deletes the image box (S39).

The command processor 147 also resets the variable Image_num indicating the number of received image data items to the initial value "0" (S40), and then the process ends.

After all the image data items to be processed have been sent, the modality 110 as the SCU sends an A-RELEASE-RQ PDU, which indicates association release request, as illustrated in step S15 of FIG. 8.

Next, a process performed when the image forming apparatus 130 receives an A-RELEASE-RQ PDU will be described.

According to the DICOM standard, any SCUs can send an A-RELEASE-RQ PDU. When the image forming apparatus 130 provides a Print SCP, a Verification SCP, and a Storage SCP as in this embodiment, the image forming apparatus 130 operates as follows. When the image forming apparatus 130 receives an A-RELEASE-RQ PDU from a Print SCU or a Verification SCU, it simply sends a response (A-RELEASE-RP PDU) to the requesting SCU. On the other hand, when the image forming apparatus 130 receives an A-RELEASE-RQ PDU from a Storage SCU, if unprinted image data remains in the image box, the image forming apparatus 130 needs to return a response after printing the image data. This process will be described below.

Figure 13:
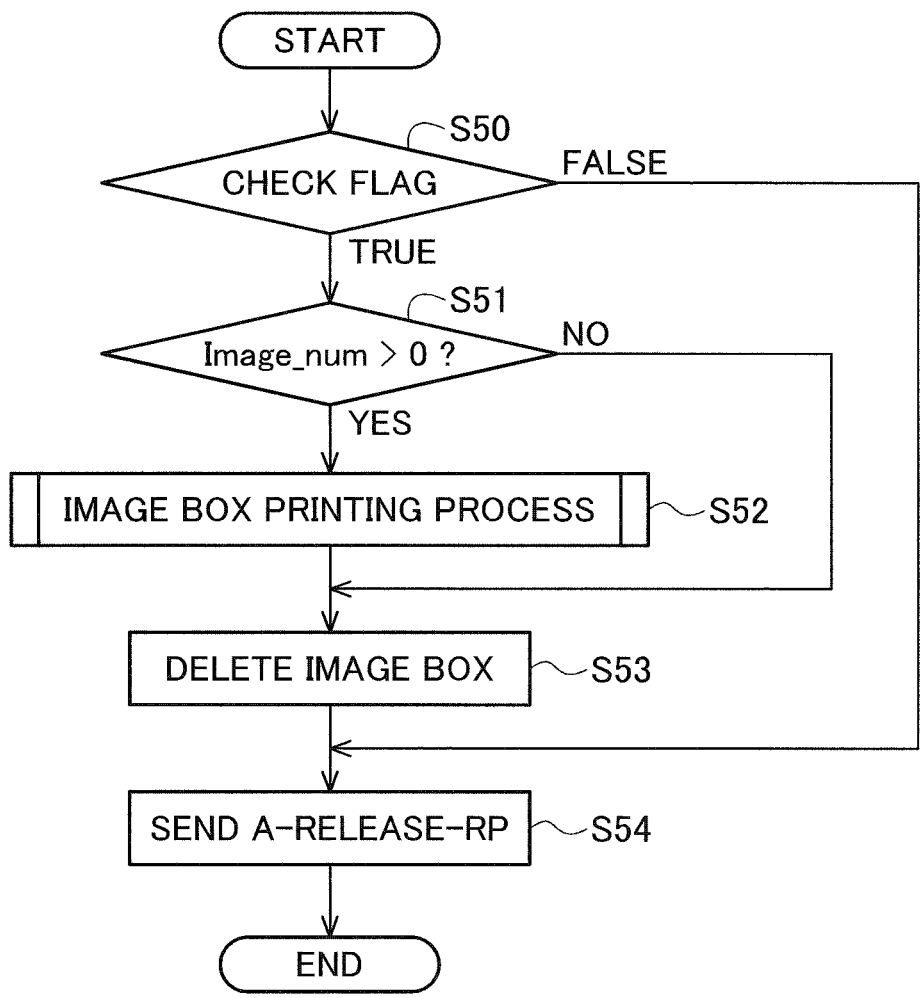
FIG. 13 is a flowchart illustrating a process by an A-RELEASE-RQ processor.

FIG. 13 is a flowchart illustrating a process by the A-RELEASE-RQ processor 149.

First, to determine whether the request is from a Storage SCU, the A-RELEASE-RQ processor 149 checks the internal flag indicating whether the request is from a Storage SCU (S50). If the internal flag is "True", which indicates that the request is from a Storage SCU, the process proceeds to step S51. If the internal flag is "False", which indicates that the request is not from a Storage SCU, the process proceeds to step S54.

In step S51, the A-RELEASE-RQ processor 149 determines whether unprinted image data remains. For example, if the variable Image_num indicating the number of received image data items is not less than 1, the A-RELEASE-RQ processor 149 determines that unprinted image data remains. If unprinted image data remains (YES in step S51), the process proceeds to step S52; otherwise (NO in step S51), the process proceeds to step S53.

In step S52, since unprinted image data remains, the image box printing process is performed. This process will be described later with reference to FIG. 14.

In step S53, the A-RELEASE-RQ processor 149 deletes the image box.

In step S54, the A-RELEASE-RQ processor 149 causes the communication unit 131 to send an A-RELEASE-RP PDU to the modality 110. Then, the process ends.

Next, the image box printing process, which can be invoked by the command processor 147 and A-RELEASE-RQ processor 149, will be described.

Figure 14:
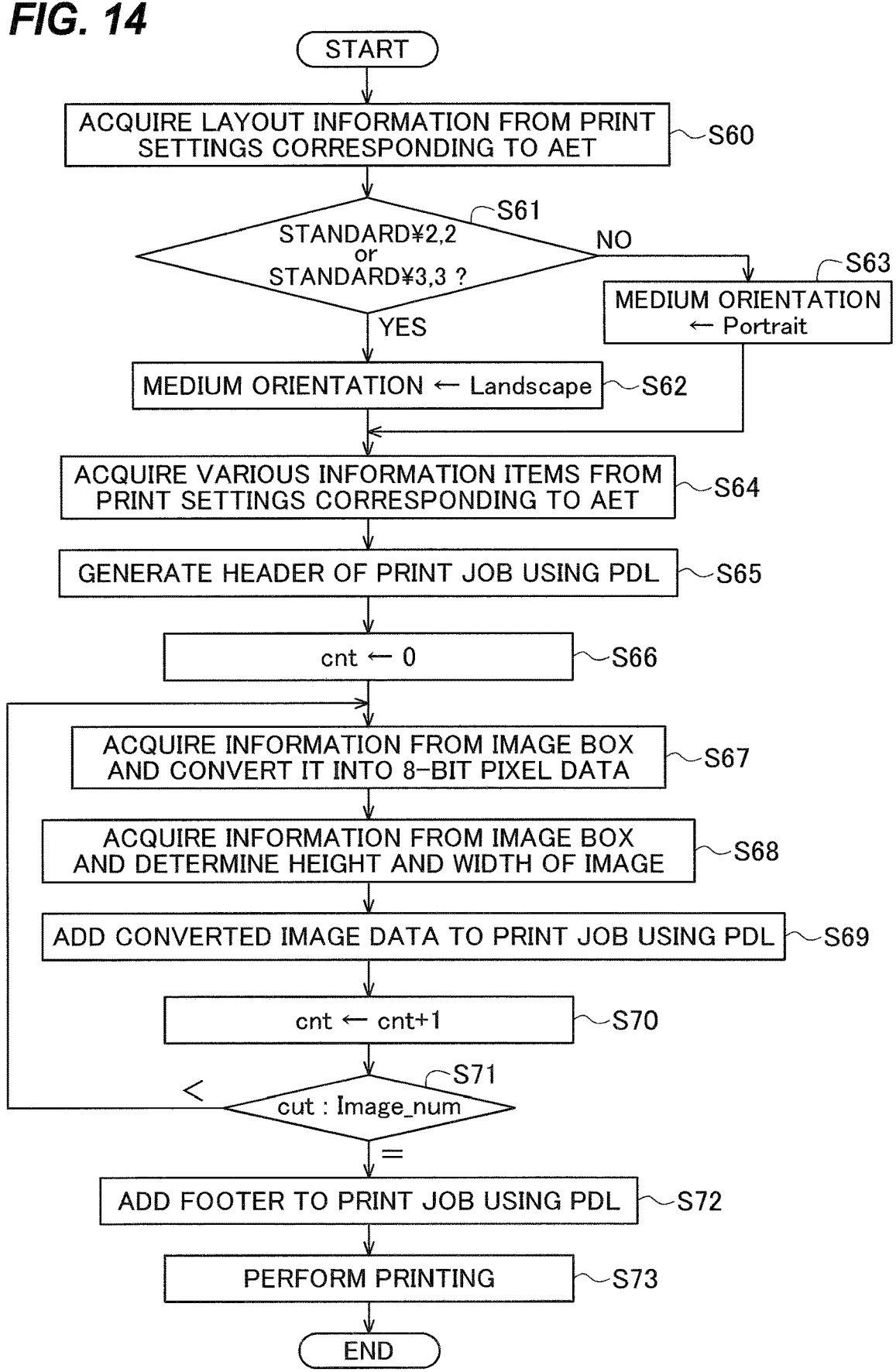
FIG. 14 is a flowchart illustrating an image box printing process.

FIG. 14 is a flowchart illustrating the image box printing process.

The image box printing process is performed by the print job generator 148.

The print job generator 148 acquires the layout information from the print settings stored in the storage unit 132 in association with the AET name included in the A-ASSOCIATE-RQ PDU received in step S11 of FIG. 8 (S60).

The print job generator 148 then determines whether the layout information acquired in step S60 is one of "STANDARD¥2,2" and "STANDARD¥3,3" (S61). If the layout information is either "STANDARD¥2,2" or "STANDARD¥3,3" (YES in step S61), the process proceeds to step S62. If the layout information is neither "STANDARD¥2,2" nor "STANDARD¥3,3" (NO in step S62), the process proceeds to step S63.

In step S62, the print job generator 148 sets the medium orientation to landscape, and then the process proceeds to step S64.

On the other hand, in step S63, the print job generator 148 sets the medium orientation to portrait, and then the process proceeds to step S64.

Since image data is mainly intended to be displayed on a display, image data is landscape in many cases. Thus, the medium orientation is set as in steps S62 and S63.

In step S64, the print job generator 148 acquires the information (i.e., settings) for the sheet tray, sheet size, number of copies, boundary frame color, and vacant frame color, from the print settings stored in the storage unit 132 in association with the AET name included in the A-ASSOCIATE-RQ PDU received in step S11 of FIG. 8.

The print job generator 148 then generates a header portion of a print job using the PDL, on the basis of the information acquired in steps S62 to S64 (S65). The print job generator 148 then allocates image data items in a page in subsequent steps.

The print job generator 148 resets a variable cnt indicating the number of image data items that have already been allocated (S66). Here, the variable cnt is set to "0".

The print job generator 148 then specifies an image data item that has not yet been allocated, acquires the various data items for the specified image data item stored in the image box 166, and converts the acquired data items into 8-bit pixel data (S67).

The print job generator 148 then determines the height and width of the image appropriate for the layout (S68).

The print job generator 148 then adds the converted image data item to the print job using the PDL (S69).

The print job generator 148 then adds 1 to the variable cnt (S70). Thereby, processing of the image data item corresponding to cnt stored in the image box 166 finishes.

The print job generator 148 then compares the variable cnt indicating the number of allocated image data items with the variable Image_num indicating the number of received image data items (S71). If the two variables are equal, the process proceeds to step S72. If the two variables are not equal, the process returns to step S67 and the process from steps S67 to S70 is repeated. Thus, the process from steps S67 to S70 is repeated the number of times corresponding to the number of image data items stored in the image box 166.

In step S72, the print job generator 148 adds a footer to the print job using PDL to complete the print job.

The print job generator 148 then provides the generated print job to the printing unit 133, thereby causing the printing unit 133 to perform printing (S73).

After the release of the association, the SCU disconnects the TCP/IP connection as illustrated in step S17 of FIG. 8, and the series of processes ends.

As described above, the image forming apparatus 130 receives the image storage request from the Storage SCU and performs printing.

When the image forming apparatus 130 receives a request from a Verification SCU or Print SCU, the image forming apparatus 130 sets, by the A-ASSOCIATE-RQ processor 144, the internal flag indicating whether the request is from a Storage SCU to "False" (S22) as illustrated in FIG. 9, and then perform a process, which may be a known process.

For example, in the case of a Verification SCU, after establishment of a TCP/IP connection, an A-ASSOCIATE-RQ PDU specifying Verification SOP Class as an abstract syntax is sent; after that, a C-ECHO-RQ command is sent and received, and then A-RELEASE-RQ PDU is sent.

In the case of a Print SCU, after establishment of a TCP/IP connection, an A-ASSOCIATE-RQ PDU specifying Basic Grayscale Print Management Meta SOP Class or Basic Color Print Management Meta SOP Class as an abstract syntax is sent; after that, various commands (N-GET-RQ, N-CREATE-RQ, N-SET-RQ, N-ACTION-RQ, N-DELETE-RQ) are sent and received, and then A-RELEASE-RQ PDU is sent.

The process by the A-ASSOCIATE-RQ processor 144 and the process by the A-RELEASE-RQ processor 149 are common to requests from Verification, Print, and Storage SCUs. With the internal flag that indicates whether the request is from a Storage SCU and that is set by the A-ASSOCIATE-RQ processor 144 and the abstract syntax list 165 illustrated in FIG. 10, requests from SCUs are appropriately processed without conflict.

Figure 15A:
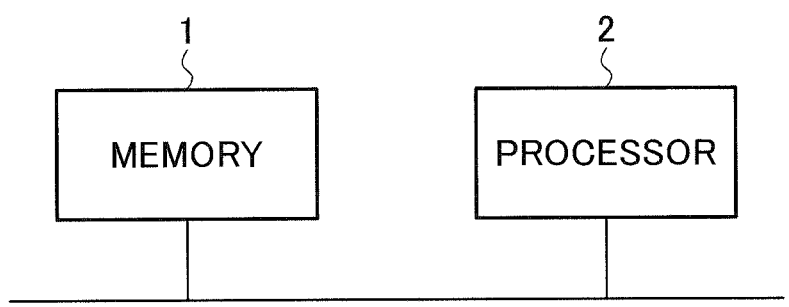
FIGS. 15A and 15B are schematic diagrams each illustrating an example of a hardware configuration of a controller.

A part or the whole of the controller 140 of the image forming apparatus 130 may be implemented by, for example, a memory 1 and a processor 2, such as a central processing unit (CPU), that executes a program stored in the memory 1, as illustrated in FIG. 15A. Such a program may be provided through a network, or may be stored in and provided from a recording medium (or computer-readable medium).

The storage unit 132 may be the memory 1 or other storage devices.

Figure 15B:
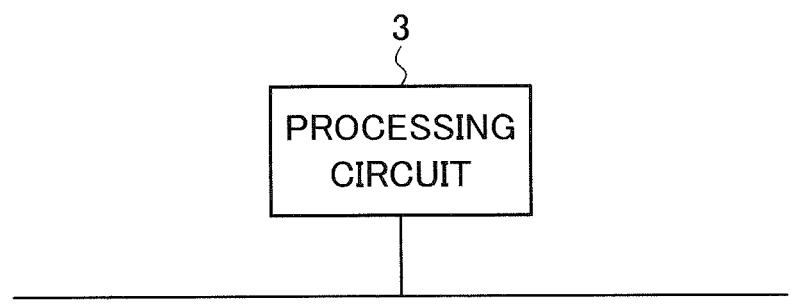

Further, a part or the whole of the controller 140 of the image forming apparatus 130 may be implemented by, for example, a processing circuit 3, such as a single circuit, a combined circuit, a programmed processor, a parallel-programmed processor, an application specific integrated circuit (ASIC), or a field programmable gate array (FPGA), as illustrated in FIG. 15B.

According to the above embodiment, even when the modality 110 has no Print SCU, in other words, even when the modality 110 is incapable of requesting printing (or incapable of issuing a request for printing), the modality 110 can obtain a product printed according to a preferred print settings without storing image data into a medical image server (not illustrated), by directly sending image data and a request for storage to the image forming apparatus 130.

The present invention is not limited to the embodiment described above; it can be practiced in various other aspects without departing from the invention scope.

For simplicity, in the above embodiment, the image forming apparatus 130 stores one set of print settings corresponding to one AET name. However, the image forming apparatus 130 can store multiple sets of print settings corresponding to multiple AET names by, for example, receiving input of the multiple sets of print settings corresponding to the multiple AET names through the AET setting screen 160 illustrated in FIG. 4. In this case, by selecting, on the modality 110 side, an AET name to which an association request is directed, from among the multiple AET names, it is possible to obtain a product printed on the basis of a preferred print settings.

Further, in the above embodiment, the image box stores and manages image display data of group 0028 and pixel data of group 7ef0. However, the image forming apparatus 130 may be configured so that the image box can also store associated information, such as examination information (group 0008), patient information (group 0010), or image acquisition information (groups 0018 and 0020). In this case, the image forming apparatus 130 may be configured to superimpose and print the associated information on the image information (or image data) in the form of, for example, a text.

The present disclosure includes the following aspects:
1. An image forming apparatus comprising:
   a communication interface that communicates with a host apparatus capable of requesting a first process but incapable of requesting a second process;
   a memory that stores a setting for the second process in association with an identifier; and
   a processor that, when the communication interface receives the identifier, image data, and a request for the first process from the host apparatus, performs the second process on a basis of the received image data according to the setting stored in association with the received identifier.
2. The image forming apparatus of aspect 1, wherein when the communication interface receives the identifier from the host apparatus, the processor performs the second process instead of the first process.
3. The image forming apparatus of aspect 1 or 2, further comprising a setting receiver that receives a setting for the second process and an identifier, and stores, in the memory, the received setting as the stored setting in association with the received identifier as the stored identifier.
4. The image forming apparatus of any one of aspects 1 to 3, wherein when the communication interface receives an identifier from the host apparatus, if the received identifier does not match the identifier stored in the memory, the processor rejects reception of the image data by the communication interface.
5. The image forming apparatus of any one of aspects 1 to 4, wherein the first process is a process of storing data.
6. The image forming apparatus of any one of aspects 1 to 5, wherein the second process is a process of forming an image based on the image data on a medium.
7. The image forming apparatus of aspect 6, wherein:
   the communication interface further receives information associated with the image data, and
   the processor superimposes the received information on the image.
8. The image forming apparatus of any one of aspects 1 to 7, wherein the host apparatus is incapable of requesting printing as the first process.
9. The image forming apparatus of any one of aspects 1 to 8, wherein:
   the image data is medical image data captured by a modality compliant with a Digital Imaging and Communication in Medicine (DICOM) standard, and
   the host apparatus is a modality.
10. The image forming apparatus of aspect 9, wherein the identifier is an Application Entity Title (AET) name.
11. The image forming apparatus of any one of aspects 1 to 10, wherein:
    the setting is one of a plurality of settings for the second process,
    the memory stores the plurality of settings in association with the identifier, and
    the processor performs the second process on a basis of the received image data according to the plurality of settings stored in association with the received identifier.
12. The image forming apparatus of aspect 11, wherein:
    the second process is a process of forming an image based on the image data on one or more media fed from a tray, and
    the plurality of settings include a setting specifying the tray, a setting specifying a size of the media, and a setting specifying a number of the media.
13. The image forming apparatus of aspect 11, wherein:
    the second process is a process of forming one or more images based on the image data on a medium, and
    the plurality of settings include a setting specifying a layout of the images on the medium.
14. The image forming apparatus of any one of aspects 1 to 10, wherein:
    the setting is one of a plurality of settings for the second process, and the identifier is one of a plurality of identifiers for identifying the plurality of settings,
    for each of the plurality of settings, the memory stores the setting in association with the identifier for identifying the setting, and
    when the communication interface receives one of the plurality of identifiers, the image data, and the request for the first process from the host apparatus, the processor performs the second process on a basis of the received image data according to the setting stored in association with the received identifier.

What is claimed is:
1. An image forming apparatus capable of communicating with a modality, the image forming apparatus comprising:
   a memory that stores a setting for a first process in association with an identifier;
   a receiver that receives the identifier, medical image data, and a request for a second process of the medical image data sent from the modality; and
   a processor that, when the identifier received from the modality that has sent the request for the second process of the medical image data to the image forming apparatus is stored in the memory, performs the first process on a basis of the medical image data for which the second process is requested by the received request for the second process of the medical image data, according to the setting for the first process stored in association with the received identifier, wherein:
   the first process is printing,
   the second process is storage, and
   when the identifier received from the modality that has sent the request for storage of the medical image data to the image forming apparatus is stored in the memory and the modality that has sent the medical image data is a Storage Service Class User (SCU), the processor performs printing of the medical image data for which storage is requested by the received request for storage of the medical image data, according to the setting for printing stored in association with the received identifier.

2. The image forming apparatus of claim 1, wherein the memory receives the setting for the first process and the identifier, and stores the setting in association with the identifier.

3. The image forming apparatus of claim 1, wherein when the identifier received by the receiver does not match the identifier stored in the memory, the processor rejects reception of the medical image data by the receiver.

4. The image forming apparatus of claim 1, wherein:
the receiver further receives information associated with the medical image data, and
the processor superimposes the information on the medical image data.

5. The image forming apparatus of claim 1, wherein the modality is an apparatus incapable of requesting printing as the second process.

6. The image forming apparatus of claim 1, wherein:
the medical image data is medical image data captured by a modality compliant with a Digital Imaging and Communication in Medicine (DICOM) standard.

7. The image forming apparatus of claim 1, wherein the identifier is an Application Entity Title (AET) name.

8. The image forming apparatus of claim 1, wherein:
the setting is one of a plurality of settings for the first process, and
the memory stores the plurality of settings in association with the identifier.

9. The image forming apparatus of claim 8, wherein:
the first process is printing on one or more media fed from a tray, and
the plurality of settings include a setting specifying the tray, a setting specifying a size of the media, and a setting specifying a number of the media.

10. The image forming apparatus of claim 1, wherein:
the setting is one of a plurality of settings for the first process, and the identifier is one of a plurality of identifiers for identifying the plurality of settings,
for each of the plurality of settings, the memory stores the setting in association with the identifier for identifying the setting,
before receiving the request for the second process, the receiver receives the identifier from the modality, and
the processor performs the first process on a basis of the medical image data according to the setting stored in association with the identifier received by the receiver.

11. The image forming apparatus of claim 1, wherein the processor determines whether the modality is the Storage SCU, on a basis of a unique identifier (UID) received from the modality.

12. The image forming apparatus of claim 1, wherein:
the processor deletes the medical image data after performing printing of the medical image data for which storage is requested by the received request for storage of the medical image data.

13. The image forming apparatus of claim 1, wherein the receiver directly communicates with the modality.

14. The image forming apparatus of claim 1, wherein:
the image forming apparatus is further capable of communicating with an information processing apparatus,
the image forming apparatus comprises a web server that allows the setting for the first process to be stored in the memory in association with the identifier, and
the processor receives the setting for the first process and the identifier from the information processing apparatus through the web server, and stores, in the memory, the received setting in association with the received identifier.

* * * * *